United States Patent
Thalmann et al.

(10) Patent No.: US 8,870,822 B2
(45) Date of Patent: Oct. 28, 2014

(54) INSERTION DEVICE FOR INSERTION HEADS AND INFUSION SETS

(75) Inventors: Christian Thalmann, Kehrsiten (CH); Simon Scheurer, Bern (CH); Martin Wyss, Burgdorf (CH)

(73) Assignee: Roche Diagnostics International AG, Rotkreuz (CH)

( * ) Notice: Subject to any disclaimer, the term of this patent is extended or adjusted under 35 U.S.C. 154(b) by 199 days.

(21) Appl. No.: 12/391,513

(22) Filed: Feb. 24, 2009

(65) Prior Publication Data

US 2009/0216215 A1 Aug. 27, 2009

Related U.S. Application Data

(63) Continuation of application No. PCT/CH2007/000400, filed on Aug. 16, 2007.

(30) Foreign Application Priority Data

Aug. 24, 2006 (CH) ...................................... 1349/06

(51) Int. Cl.
*A61M 5/20* (2006.01)
*A61M 25/06* (2006.01)
*A61M 5/158* (2006.01)
*A61M 5/32* (2006.01)

(52) U.S. Cl.
CPC ....... *A61M 5/158* (2013.01); *A61M 2005/1581* (2013.01); *A61M 5/3287* (2013.01); *A61M 25/0612* (2013.01); *A61M 2005/1585* (2013.01); *A61M 2005/1587* (2013.01)
USPC ........... 604/137; 604/136; 604/156; 604/157; 604/164.01; 604/164.02; 604/164.04; 604/164.06; 604/164.07; 604/164.08; 604/164.09; 604/164.1; 604/164.11; 604/164.12; 604/171

(58) Field of Classification Search
CPC .............. A61M 5/158; A61M 5/3287; A61M 2005/1587; A61M 2005/206; A61M 2005/1585
USPC ............... 604/136, 137, 164.11–164.12, 156, 604/157, 164.01, 164.02, 164.04, 604/164.06–164.1, 171
See application file for complete search history.

(56) References Cited

U.S. PATENT DOCUMENTS

| 4,403,989 | A * | 9/1983 | Christensen et al. ......... 604/137 |
| 8,303,545 | B2 * | 11/2012 | Schraga ................... 604/167.02 |
| 8,475,410 | B2 * | 7/2013 | Kaufmann et al. ........... 604/136 |
| 8,696,625 | B2 * | 4/2014 | Carrel et al. .................. 604/117 |
| 2004/0158207 | A1 * | 8/2004 | Hunn et al. .............. 604/164.01 |

(Continued)

FOREIGN PATENT DOCUMENTS

| EP | 1 704 889 | 9/2006 |
| EP | 1 764 125 | 3/2007 |
| WO | 2004/110527 | 12/2004 |
| WO | 2004/110527 A | 12/2004 |

*Primary Examiner* — Quynh-Nhu H Vu
*Assistant Examiner* — Larry R Wilson
(74) *Attorney, Agent, or Firm* — Dinsmore & Shohl LLP

(57) ABSTRACT

An insertion device for applying an infusion set to the body of a patient, wherein the device has two actuation members which have to be actuated simultaneously to trigger an insertion movement by which a cannula of the infusion set is introduced into the body and wherein, in some embodiments, one of the actuation members is a securing slide including a contact face to be placed on the body of the patient, the securing slide being actuated by the insertion device being pressed, via the contact face, against the body of the patient.

19 Claims, 16 Drawing Sheets

(56) References Cited

U.S. PATENT DOCUMENTS

2005/0101912 A1* 5/2005 Faust et al. .................... 604/117
2005/0131347 A1* 6/2005 Marano-Ford et al. ....... 604/136
2005/0283114 A1* 12/2005 Bresina et al. ............. 604/93.01
2006/0069351 A9* 3/2006 Safabash et al. .............. 604/136
2006/0135908 A1* 6/2006 Liniger et al. ............. 604/93.01

* cited by examiner

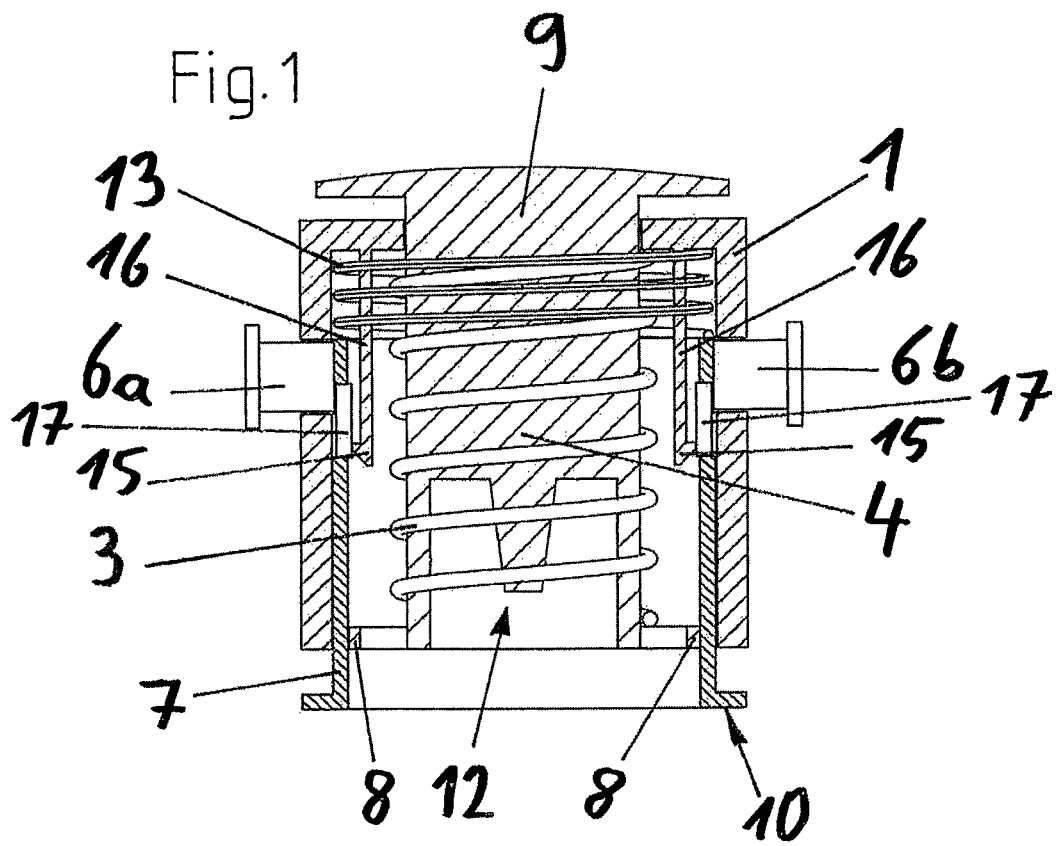
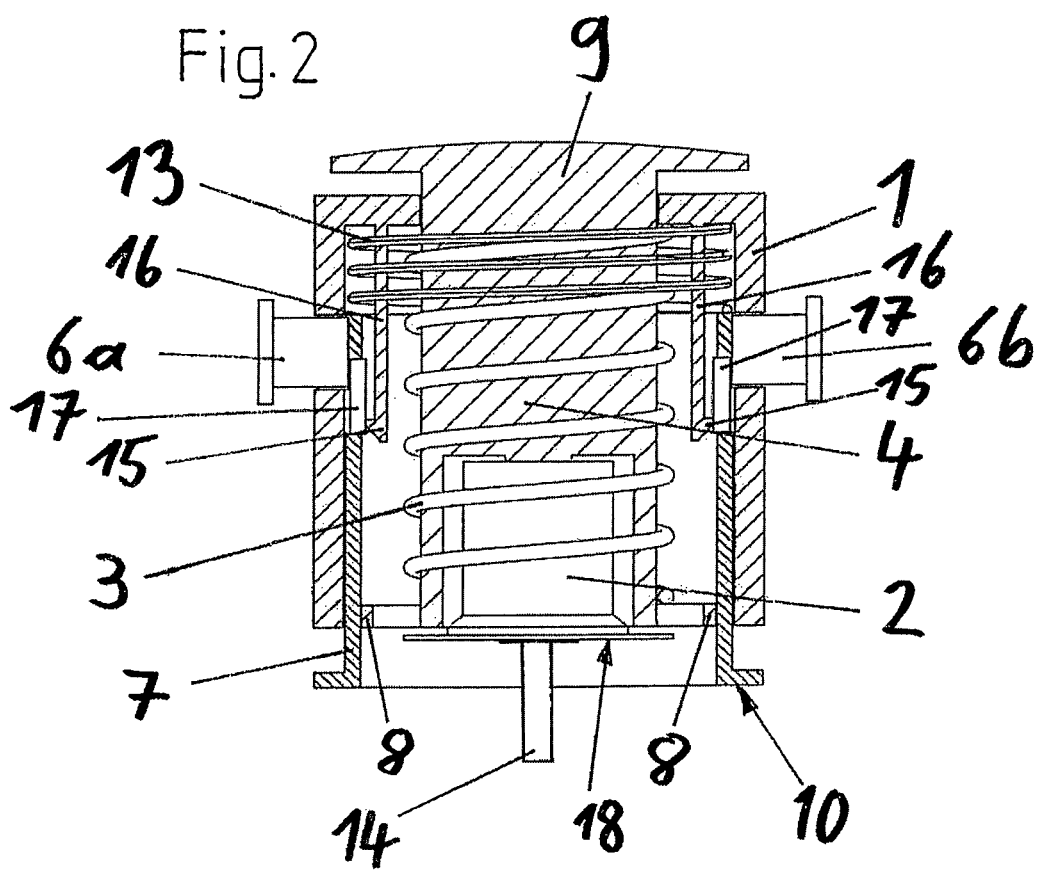

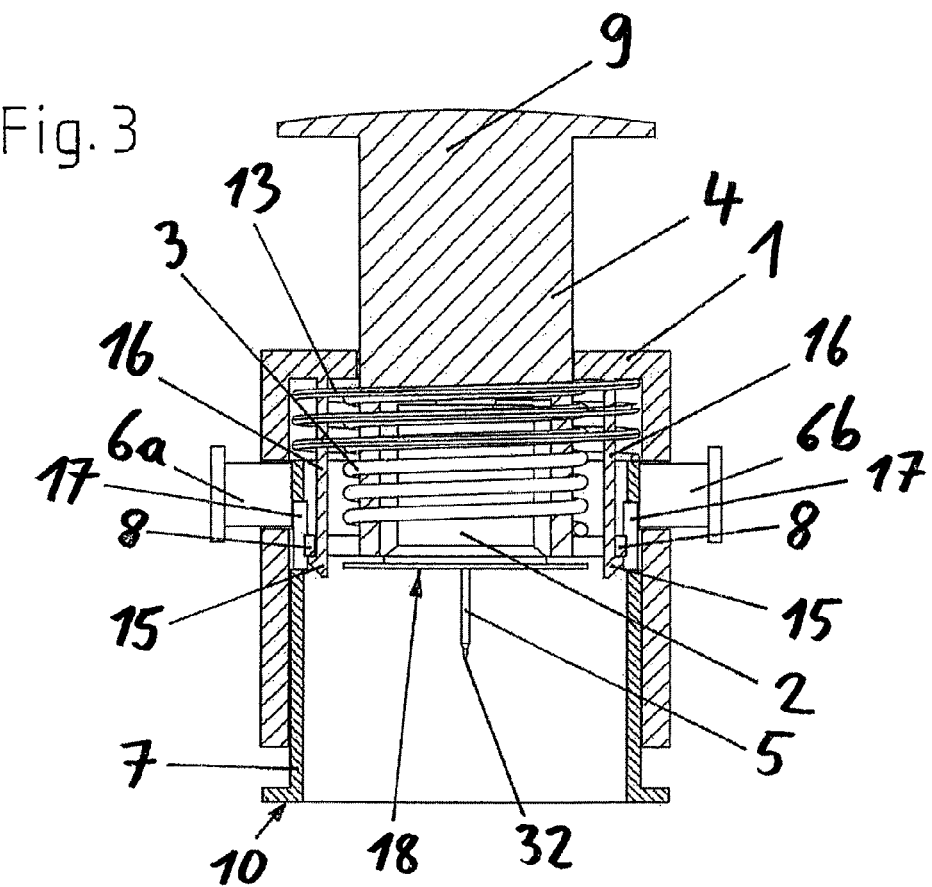
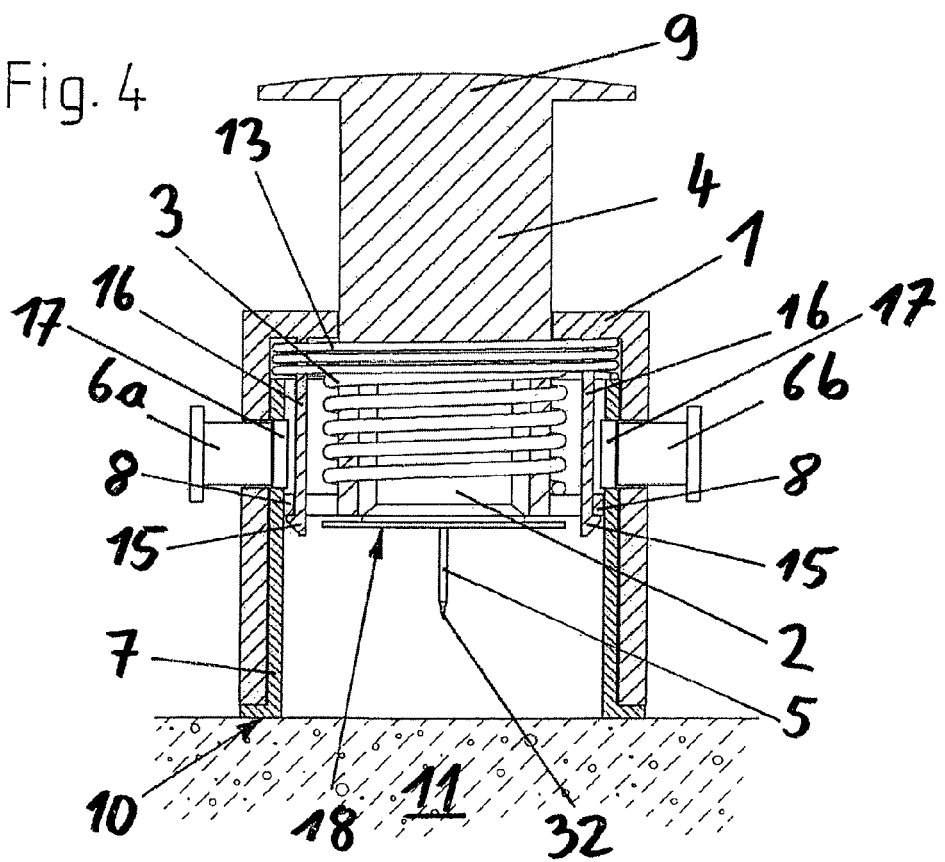

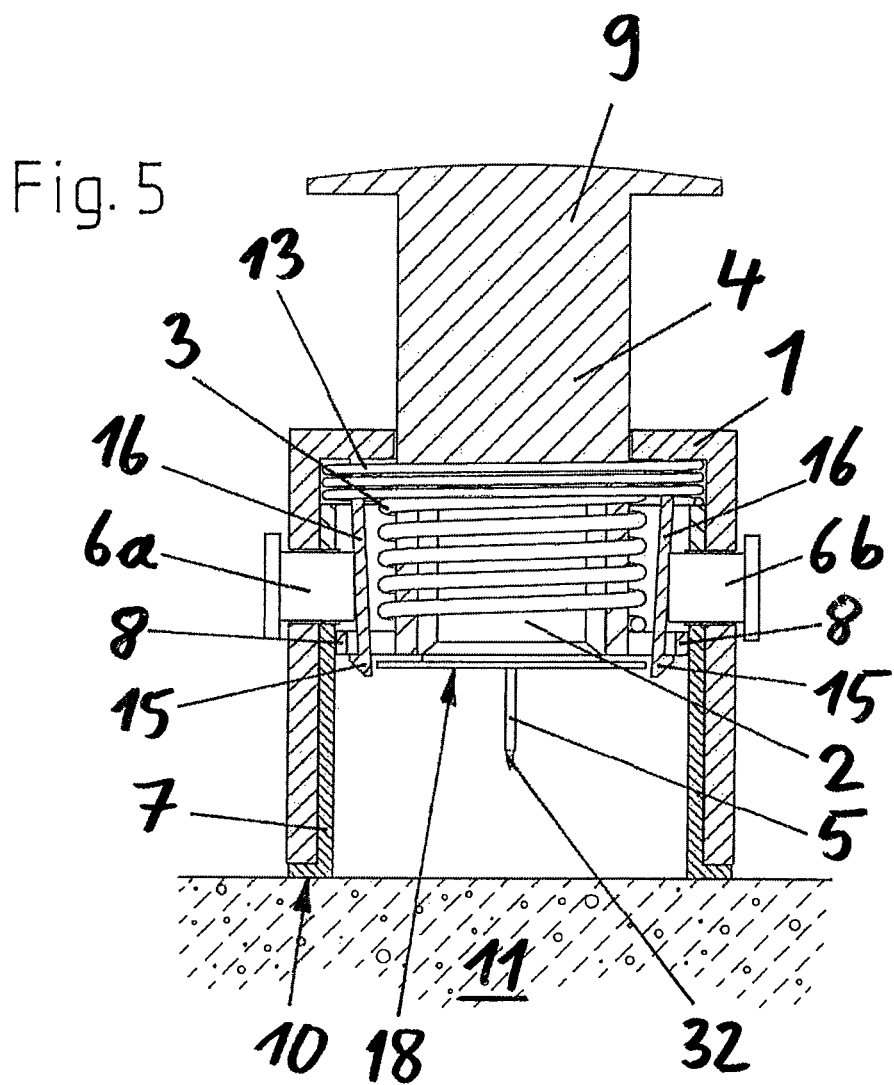

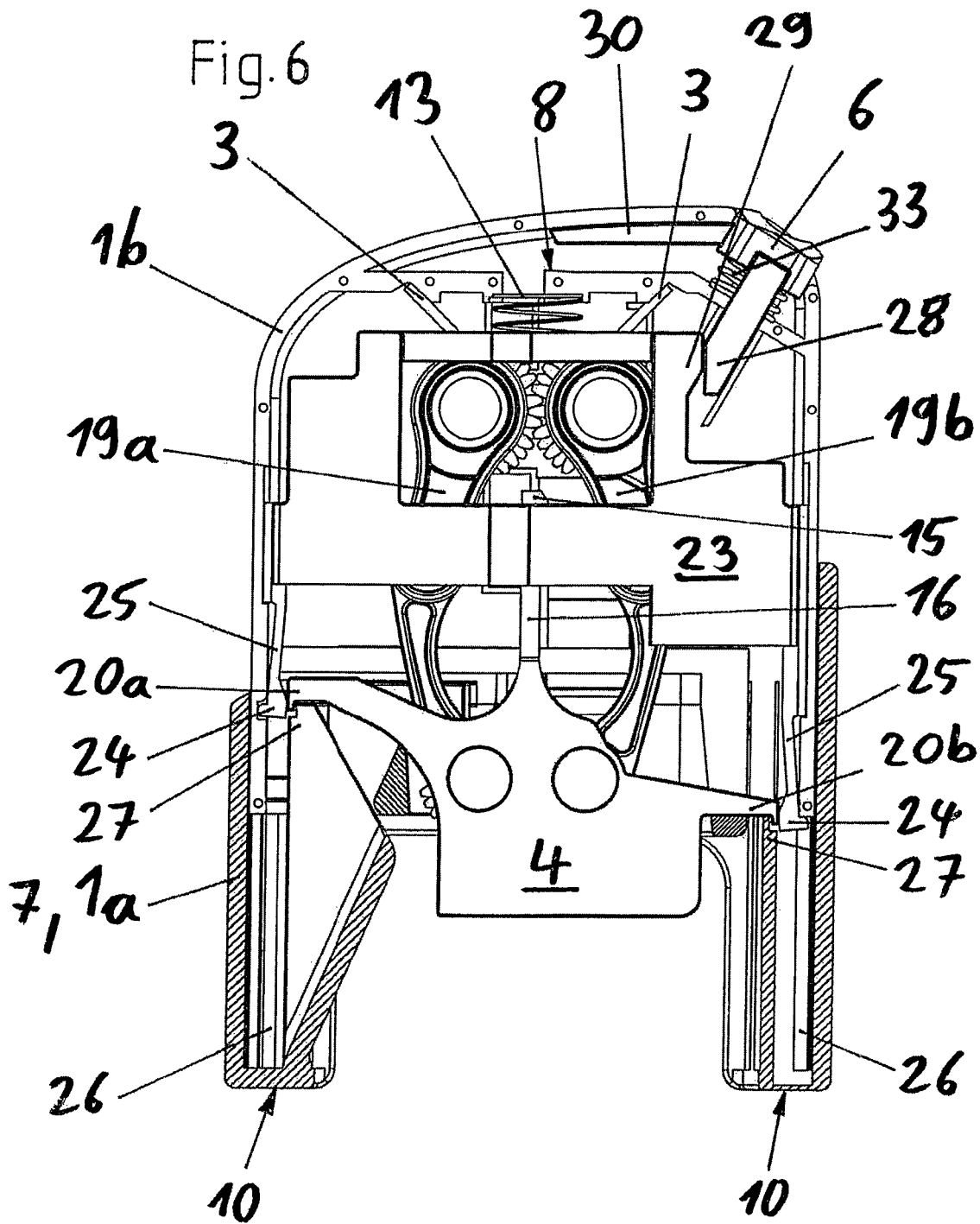

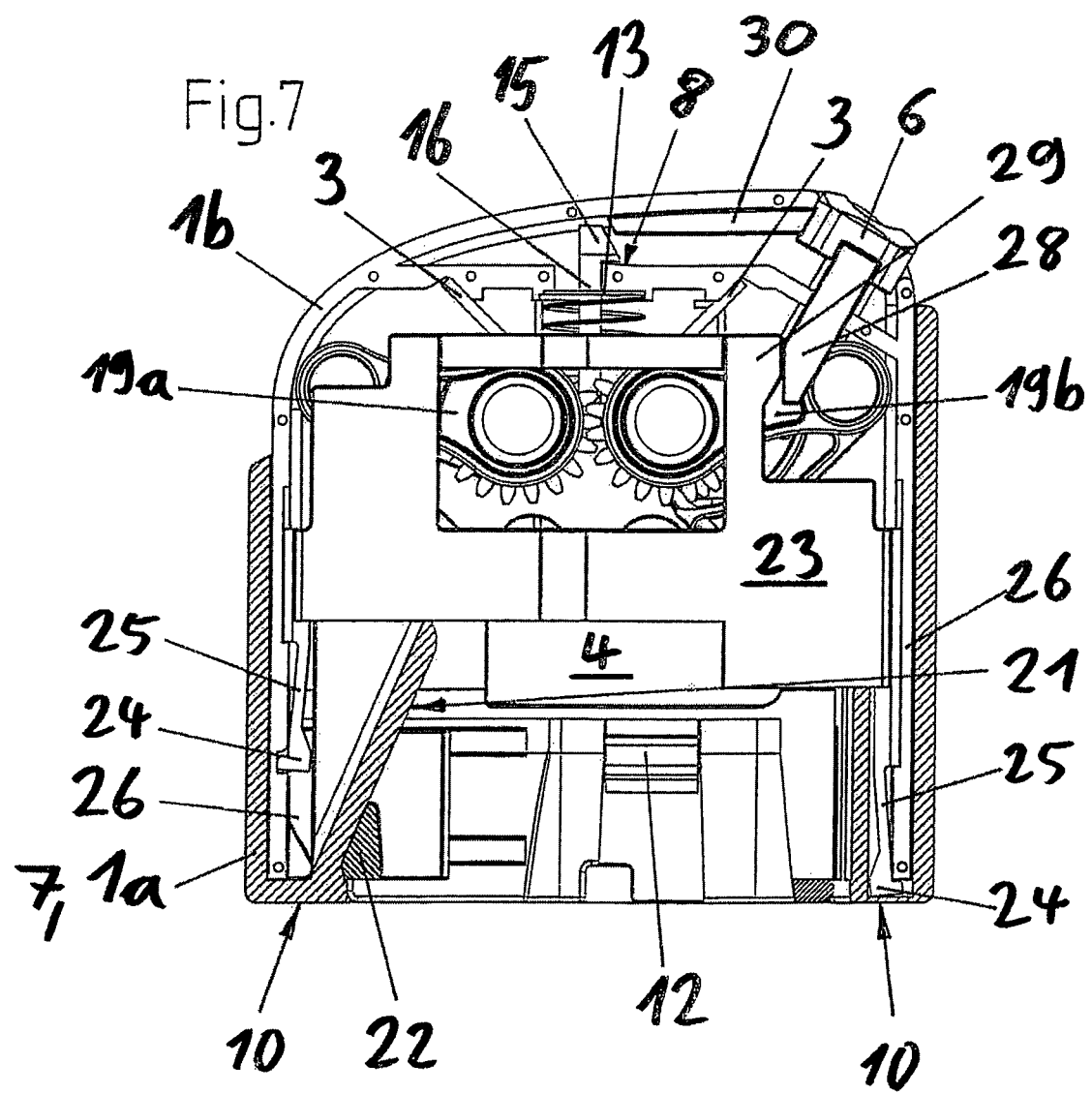

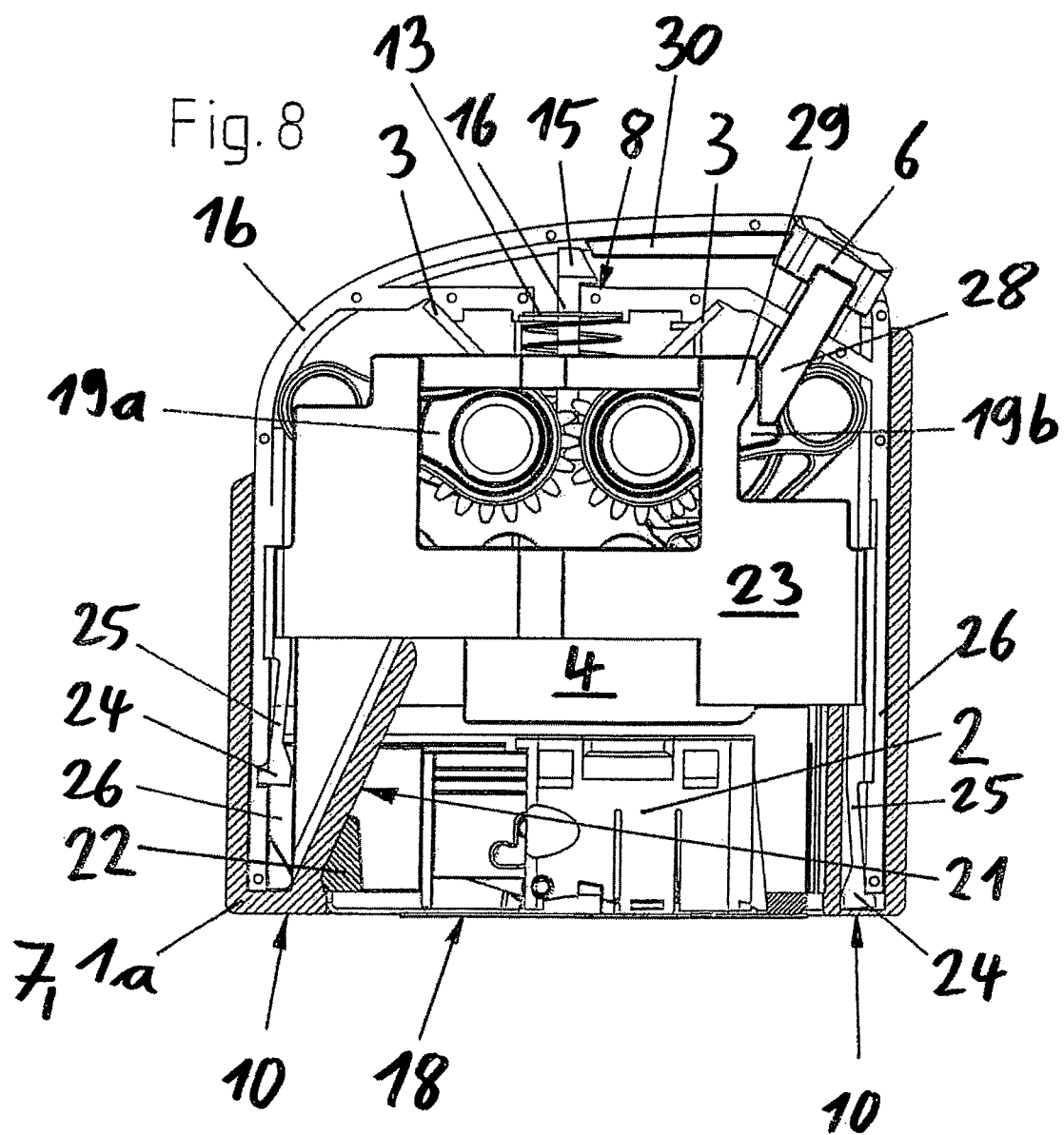

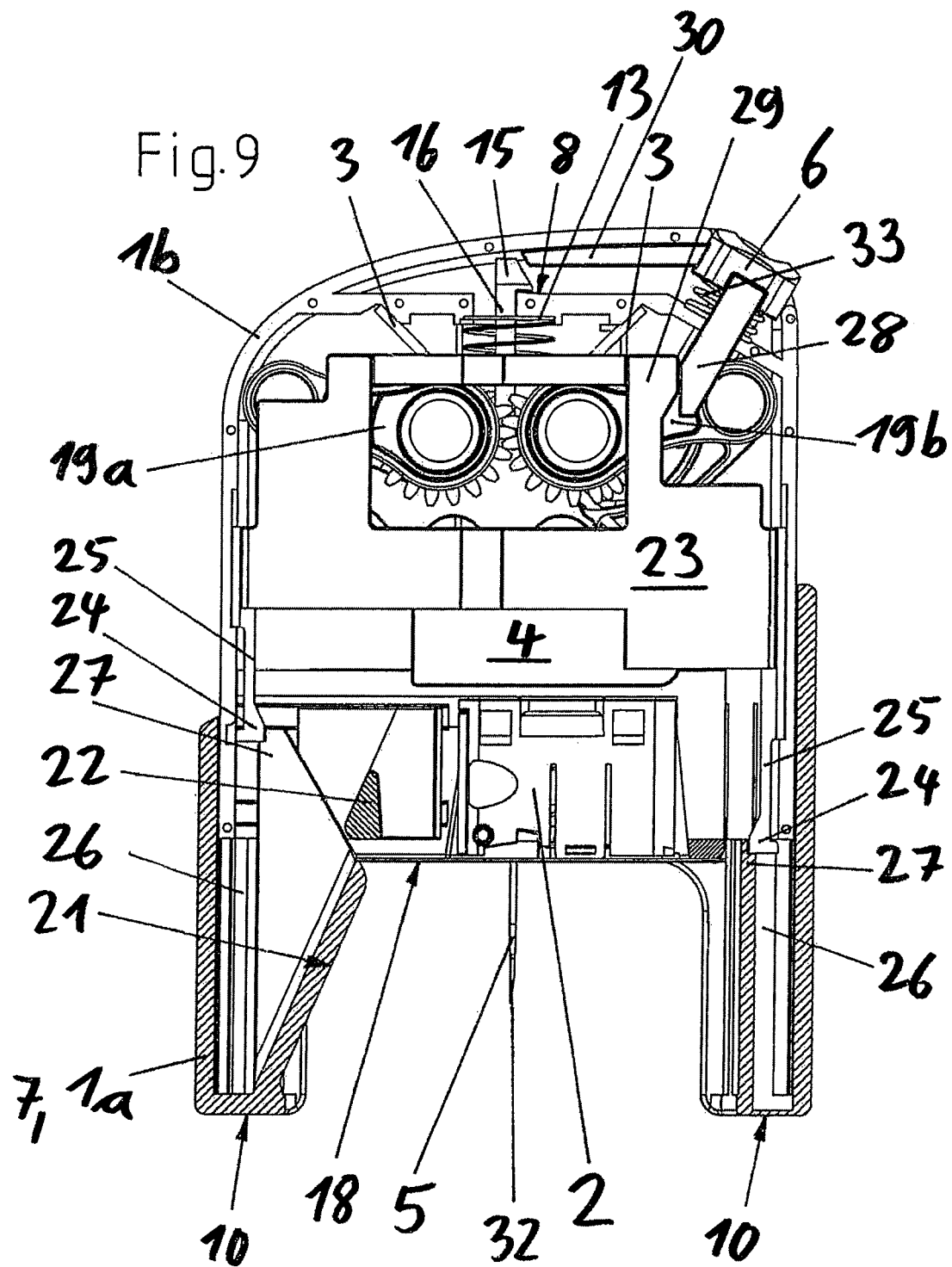

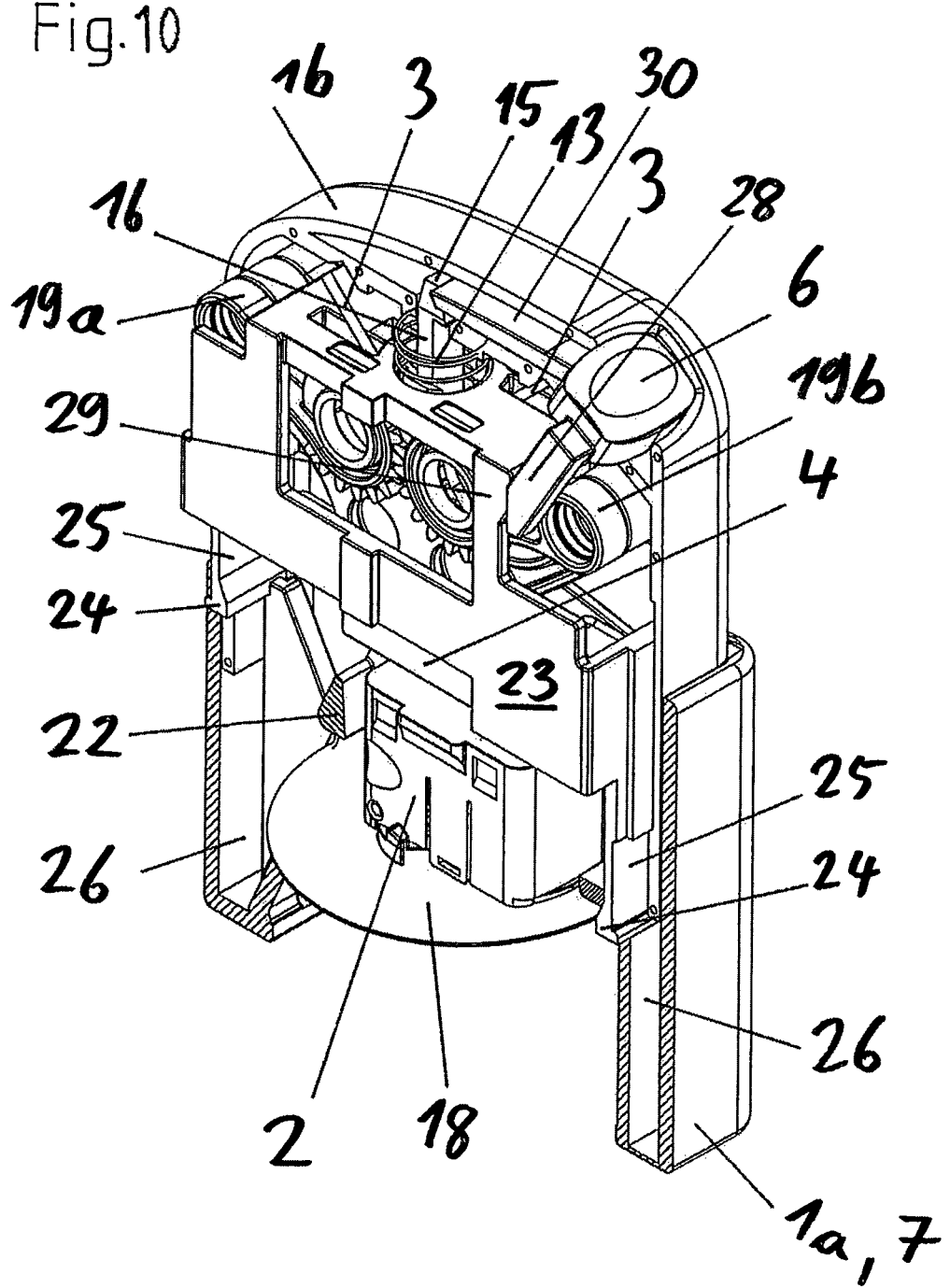

INSERTION DEVICE FOR INSERTION HEADS AND INFUSION SETS

CROSS-REFERENCE TO RELATED APPLICATIONS

This application is a continuation of International Patent Application No. PCT/CH2007/000400, filed on Aug. 16, 2007, which claims priority to Swiss Application No. 1349/06, filed on Aug. 24, 2006, the entire contents of both of which are incorporated herein by reference.

BACKGROUND

The present invention relates to devices for injecting, infusing, delivering, dispensing or administering a substance, and to methods of making and using such devices. More particularly, it relates to an insertion device for insertion heads, an arrangement comprising the insertion device, a use of the insertion device or of the arrangement, and/or a method for applying an insertion head to the body of a patient with the insertion device.

In patients with a regular requirement for a medicament that can be administered by direct delivery into the body tissue or into the blood stream, for example certain groups of patients suffering from pain, or patients with type I and type II diabetes, it can be useful to supply the body with the required quantity of medicament in liquid form via a cannula that is introduced at a suitable location into the body and that remains there over quite a long period of time. For this purpose, a cannula arrangement, designated as an infusion set or port, depending on its design, is secured on the patient's skin, in such a way that the cannula passes through the skin and into the body.

Efforts are also increasingly being made to monitor certain medical parameters of a patient, for example the blood sugar value, continuously over quite a long period of time. For this purpose, a sensor arrangement, for example, is placed on the patient's body and, with a puncturing tip of a suitable sensor, passes through the skin and into the patient's body.

To avoid infections, the infusion set, the port or the sensor arrangement has to be changed at regular intervals, for example every three days. In outpatient treatment, for example in the case of diabetics, this is often done by the patients themselves and, on account of the introduction of the infusion cannula or of the puncturing tip into the skin, is associated with a certain amount of pain. It is therefore important that such infusion sets, ports or sensor arrangements can be applied easily and safely, which is why many manufacturers have started designing their products as insertion heads for special insertion devices with the aid of which the insertion heads can be applied to the patient's body. Application is made easier in this way, and the pain occasioned by the application is reduced to a minimum, thanks to the quick and targeted puncturing procedure.

Thus, for example, U.S. Pat. No. 6,607,509 B2 discloses insertion devices for infusion sets, in which the infusion set is placed abruptly onto the application site by the force of a pretensioned spring, and the cannula penetrates into the tissue of the patient. The insertion device is in this case triggered by actuation of a trigger button that is arranged at one end and that can be locked and unlocked by turning it, or by simultaneous actuation of two radial trigger buttons lying opposite one another.

WO 03/026728 A1 discloses similar insertion devices triggered by pressing two retention arms with locking lugs together or by pressing a trigger button.

WO 2004/110527 A1 also discloses similar insertion devices for infusion sets, in which the triggering is effected by actuation of a single trigger button that is arranged at one end and that can be alternately locked and unlocked by pivoting of a safety lever, or by simultaneous actuation of two trigger buttons lying opposite one another.

All of the above-noted known insertion devices have the disadvantage that they are not secured, or are only inadequately secured, against inadvertent triggering, since any safety devices, if indeed any are present at all, are often not even activated, or are already deactivated before the insertion device is placed on the application site. There is, therefore, considerable danger that a user will accidentally trigger the insertion device and sustain an injury, for example from the infusion cannula of the infusion set that is to be applied, or from the puncturing tip of the sensor arrangement that is to be applied.

SUMMARY

An object of the present invention is therefore to provide an insertion device for insertion heads, wherein the insertion device does not have, or at least partially avoids, the disadvantages of known devices.

In one embodiment, the present invention comprises an insertion device for applying an infusion set to the body of a patient, wherein the device comprises two actuation members which have to be actuated simultaneously to trigger an insertion movement by which a cannula of the infusion set is introduced into the body and wherein, in some embodiments, one of the actuation members is a securing slide including a contact face to be placed on the body of the patient, the securing slide being actuated by the insertion device being pressed, via the contact face, against the body of the patient.

In some embodiments, the present invention concerns an insertion device for insertion heads, which can be designed, for example, as an infusion set, port or sensor arrangement, for example for measuring the blood sugar value, the insertion device having one or more contact faces, which are formed, for example, by a housing of the device and with which the insertion device is placed onto the skin of the patient for application of the insertion head.

The insertion device also comprises retainers or retention means with which the insertion head to be applied can be temporarily held on the insertion device, with the result that, during the actual application of the insertion head, only the insertion device has to be held by the user at the application site.

The insertion device, ready for application, moreover comprises drive means with which the insertion head to be applied can be moved relative to the contact face in the longitudinal direction of the infusion cannula or of the puncturing tip. The insertion head is moved from a first position, in which it is held by the retention means in such a way that its infusion cannula or puncturing tip is set back relative to the contact face for avoiding inadvertent contact with the user, to a second position in which the infusion cannula or the puncturing tip protrudes substantially completely beyond the contact face, to permit introduction of the infusion cannula or of the puncturing tip into the body of the patient when the insertion device is placed with the contact face on the skin of the patient. This movement of the insertion head, by which it is actually applied to the body, may be referred to or thought of as an insertion movement.

The insertion device further comprises at least two actuation members which have to be actuated simultaneously to trigger the insertion movement. A first of the actuation members is designed such that it can be actuated by pressing the contact face of the insertion device onto the body of the patient, e.g. by it being pressed in the direction of the insertion movement. Thus, the insertion device considerably reduces the danger of accidental triggering of the insertion device when ready for application, and thus considerably reduces the chance of the user sustaining an injury.

In a preferred embodiment of the insertion device, the actuation members, which have to be actuated simultaneously to trigger the insertion movement, are designed such that, when an actuating force ceases, they automatically readopt their unactuated state. It is possible in this way to further increase the safety against inadvertent triggering of the insertion device.

In another preferred embodiment of the insertion device, the first actuation member is designed as a slide-shaped or button-shaped element. In some preferred embodiments, the latter at the same time forms the entire contact face or, if there are several contact faces, forms all the contact faces. The advantage of this is that it permits reliable actuation of the first actuation member independently of the surface contour of the application site on the body of the patient.

In yet another preferred embodiment, at least one other of the actuation members is designed as a button-shaped element which can be actuated when the user presses it with a finger tip. In some preferred embodiments, the actuation direction is transverse, e.g. perpendicular, to the direction in which the insertion device is to be pressed onto the body of the patient. In some preferred embodiments, the actuation direction is the same as the direction of the insertion movement and therefore the same as the direction of introduction of the infusion cannula or of the puncturing tip. The danger of inadvertent actuation of this actuation member together with the first actuation member can be further reduced in this way, such that the danger of inadvertently triggering the insertion device is further reduced.

In some embodiments, it may also be advantageous if the actuation direction is parallel or substantially parallel to the direction of pressing.

In yet another preferred embodiment of an insertion device in accordance with the present invention, all the actuation members, which have to be actuated simultaneously to trigger the insertion movement, are designed such that they can be actuated by the user with one hand. This permits one-handed operation of the insertion device, as a result of which the insertion head can be applied by the patient even in areas of the body that are inaccessible with both hands or are difficult to access with both hands, for example in the area of the hips.

If the driver or drive means of the insertion device comprises one or more energy-storing elements for providing the drive energy for the insertion movement, for example helical springs, leg springs or leaf springs made of metal, or rubber spring elements, the insertion device can be used at any time and in any place, independently of external sources of energy, and can also be made inexpensive.

It is advantageous if the insertion device is designed such that the energy-storing element can be pretensioned by the user, including repeatedly, and made ready in the pretensioned state, such that the insertion device can be brought into a pretensioned state, ready for the application, directly before use and can also advantageously be used several times.

The driver or drive means advantageously comprise a thrust element for transmitting the drive energy to the insertion head to be applied and are designed in such a way that the energy-storing element can be pretensioned by displacing the thrust element counter to the direction of the insertion movement and by subsequently locking the thrust element with locking means that can be released by the actuation members, the energy-storing element thus being made ready in the pretensioned state. In this way, it is possible to provide reliable drive means that permit a high initial acceleration and therefore a rapid insertion movement, as a result of which the application pain occasioned upon introduction of the infusion cannula or puncturing tip into the body is minimized and/or abbreviated.

A simple and robust pretensioning mechanism is obtained if the thrust element of the energy-storing element is advantageously connected rigidly to the grip part, which can be grasped by hand and can be moved relative to the housing in order to pretension the energy-storing element.

Alternatively, in some preferred embodiments, the insertion device comprises a housing with two housing parts which can be pushed together and which are coupled to the thrust element in such a way that the latter can be moved, e.g. displaced, by a pushing-together of the two housing parts, to pretension the energy-storing element. This design variant also is user-friendly.

In yet another preferred embodiment of the insertion device according to the present invention, its actuation members, which actuated to trigger an insertion movement, are coupled to one another such that by actuating one of the actuation members, a blocking of another or several others of the actuation members can be cancelled. The construction is simplified because only a single trigger mechanism is required.

In embodiments with a housing having two housing parts, which can be pushed together and whose pushing together pretensions the energy-storing element, in some preferred embodiments the two housing parts can be drawn apart again from one another after the energy-storing element has been pretensioned. In some embodiments, they are designed such that one of the two housing parts is coupled to a lock or locking means, with which one or several actuation members of the insertion device are blocked or secured. The coupling is effected such that this blocking can be cancelled by renewed and at least partial pushing-together of the two housing parts. After being coupled to the locking means, the coupled housing part thus forms an actuation member of the insertion device. This design affords the advantage that the insertion movement can be triggered only after the two housing parts have been deliberately drawn apart again, as a result of which the safety against accidental triggering of the insertion device is increased still further.

If the thrust element, the securing means and the housing part, connected or connectable to these, are designed such that the coupling between the securing means and the housing part is cancelled again after the triggering of the insertion movement by the thrust element, which is the case in some preferred embodiments, then the insertion device is returned to its original state after correct application of an insertion head. Renewed triggering is then possible only after renewed pretensioning of the energy-storing element by pushing the housing parts together and subsequently drawing the housing parts apart again, with one housing part being able to be coupled to the locking means.

In yet another preferred embodiment of the insertion device according to the present invention, the direction of the insertion movement of the insertion head is perpendicular to a plane formed by the contact face or contact faces of the insertion device. In an alternative embodiment, the direction of the insertion movement of the insertion head is non-perpendicular to a plane formed by the contact face or contact faces of the insertion device, e.g. forms an angle with said plane of 20° to 45°. Depending on the specific application or intended use, one or the other of these embodiments might be more advantageous.

A second aspect of the present invention concerns an arrangement comprising an insertion device as described above, and an insertion head which is received or can be received in the latter and which is designed as an infusion set, port or sensor arrangement. By fitting a suitable insertion head into the insertion device an arrangement according to the present invention is achieved. In addition to the marketing of inventive and reusable insertion devices, and of associated insertion heads, such as associated infusion sets, ports or sensor arrangements, which are joined together by the user shortly before use to form arrangements according to the present invention, provision is also made for preassembled arrangements according to the present invention to be offered as disposable articles, with the insertion device being disposed of after the insertion head has been applied.

A third aspect of the invention concerns the use of the insertion device and/or arrangement according the present invention for applying an insertion head to the body of a patient. In some preferred embodiments, the insertion head is an infusion set, port, sensor arrangement, or the like. Such uses are in accordance with the present invention and bring out clearly the advantages of the invention.

A fourth aspect of the present invention concerns a method for applying an insertion head to the body of a patient, e.g. an insertion head designed as an infusion set, port or sensor arrangement, using an insertion device according to the present invention. In a first method step, the insertion device is made ready with an insertion head held in a first position by the retention means. In other words, an arrangement according to the present invention is made ready with the insertion head arranged in a first position. Then, in a second step, this arrangement is arranged with the contact face of the insertion device on the desired application site on the body of the patient such that the infusion cannula or the puncturing tip of the insertion head can penetrate correctly into the body upon the subsequent insertion movement, being pressed on in such a way that a first actuation member is actuated. In this state, the second and, if present, also any further actuation members provided for triggering the insertion device are actuated, whereupon the insertion movement is triggered. By this method, it is possible to considerably reduce the danger of the user being injured by inadvertent triggering of the insertion device.

In a preferred embodiment of the method, the arranging and pressing of the insertion device and the actuating of the second and, if present, also any further actuation members is done with one hand, such that it is possible for the patient to apply the insertion head, without help from another person, to areas of the body that are inaccessible or difficult to access with two hands.

In another preferred embodiment of the method, the insertion device is pressed onto the desired application site, on the body of the patient, in the direction of the insertion movement. This permits a reliable application procedure.

In yet another preferred embodiment of the method, the second and, if present, also any further actuation members are each actuated by the user pressing them with a finger tip, e.g. in a direction transverse to the direction in which the insertion device is pressed onto the body of the patient, thus further reducing the danger of incorrect triggering of the insertion device.

In some embodiments of the method in accordance with the present invention, it may also be advantageous if the actuation direction is parallel or substantially parallel to the pressing-on direction.

BRIEF DESCRIPTION OF THE DRAWINGS

FIG. 1 is a vertical section through an embodiment of a first insertion device according to the present invention for insertion heads, in the non-pretensioned state and without an insertion head;

FIG. 2 is a view of the insertion device of FIG. 1, but with an insertion head arranged in it;

FIG. 3 is a vertical section through the first insertion device in the pretensioned state, with an insertion head arranged in it in the secured state;

FIG. 4 is a view of the first insertion device of FIG. 3, but in the released state;

FIG. 5 is a view of the first insertion device of FIG. 4, but with the trigger buttons actuated at the moment of triggering;

FIG. 6 is a partial vertical section through another embodiment of an insertion device according to the present invention for insertion heads, in the non-pretensioned state and without an insertion head;

FIG. 7 is a view of the insertion device of FIG. 6, but in the pretensioned, secured state;

FIG. 8 is a view of the insertion device of FIG. 7, but with an insertion head designed as infusion set arranged in it, with the infusion cannula folded in;

FIG. 9 is a view of the insertion device of FIG. 8, but with the infusion cannula folded out;

FIG. 10 is a perspective view, partially in vertical section, of the insertion device of FIG. 9;

DETAILED DESCRIPTION

Figure 11:
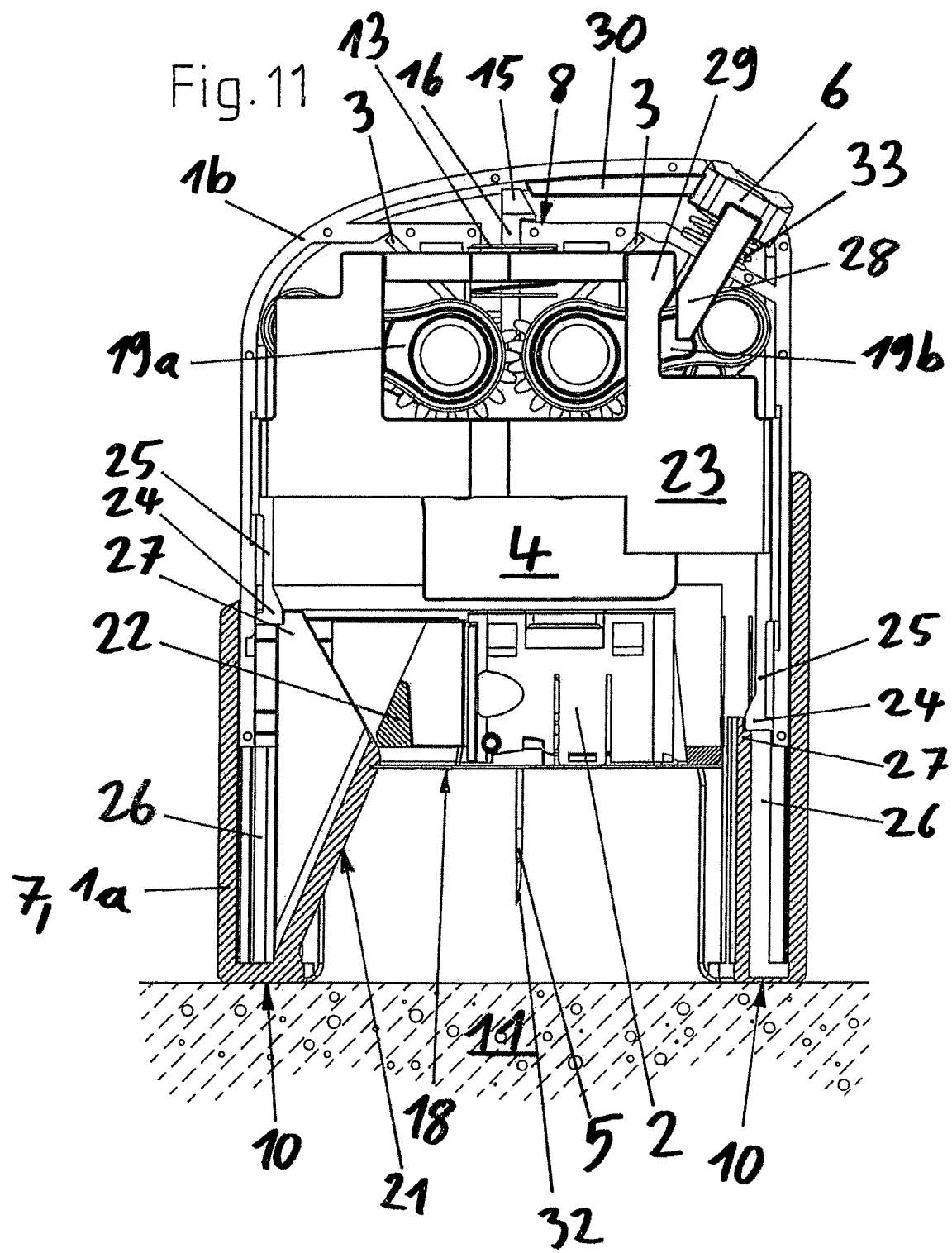
FIG. 11 is a view of the insertion device of FIG. 9, but in the released state, when placed and pressed onto the body of a patient.

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

One embodiment of an insertion device according to the present invention is shown in vertical section in FIGS. 1 to 5, in different states that arise during its intended use.

As can be seen from FIGS. 1 and 2, which show the insertion device without an insertion head (FIG. 1) and then with a fitted insertion head (FIG. 2), in a basic state in which it is not ready for application, the insertion device comprises a housing 1, a piston-like thrust element 4 arranged displaceably in the housing 1, and an energy-storing element designed as a helical spring 3 for driving the thrust element 4. On its underside, the thrust element 4 has a receptacle 12 (see FIG. 1) for force-fit attachment of the insertion head which is to be applied with the insertion device and which, in the present example, is designed as an infusion set 2 (see FIG. 2), which receptacle forms a retention means. With the infusion set 2 arranged inside the housing 1 in FIG. 2, the infusion cannula 5 (not visible here) is protected by a needle guard 14, such that in this state the user is safely protected against injury by the cannula 5. On its top face, the thrust element 4 has a grip part 9 by which it can be drawn upwards relative to the housing 1, counter to the spring force of the helical spring 3, to pretension the helical spring 3. The insertion device also comprises a first actuation member designed as a securing slide 7, and also two further actuation members which are designed as trigger buttons 6a, 6b and whose actuation, in the situation illustrated, is blocked or prevented by the securing slide 7. On its top face, the securing slide 7 is spring-loaded in a downward direction by a restoring spring 13 with force direction. On its underside, it has a circular contact face 10 via which the insertion device is placed and pressed onto the body 11 of the patient upon application of the infusion set 2.

If the insertion device according to FIG. 2 is now to be made ready in a pretensioned state, for application of the infusion set 2 received in it, as is shown in FIG. 3, the release liner of the plaster 18 is removed and the grip part 9 is pulled up such that the thrust element 4 is moved upward relative to the housing 1 counter to the force of the spring 3, until two locking shoulders 8 formed by the thrust element 4 catch on locking lugs 15 formed on two spring arms 16 integral with the housing. The helical spring 3 and the thrust element 4 are now ready in the pretensioned state and the infusion set 2 is in the first position, in which the infusion cannula 5 is arranged in the housing 1 in a set-back position relative to the contact face 10. The cannula guard 14 is now removed from the infusion cannula 5, such that the arrangement made up of the insertion device and of the infusion set 2 arranged therein is ready for application. As will be seen, an actuation movement of the two trigger buttons 6a, 6b radially inward is still made impossible by the securing slide 7.

To apply the infusion set 2, the insertion device is now pressed with the contact face 10 onto the application site on the body 11 of the patient, in such a way that the securing slide 7 slides into the housing 1 counter to the force of the restoring spring 13 and, in doing so, brings two openings 17 formed in it into alignment with the trigger buttons 6a, 6b, through which openings 17 the trigger buttons 6a, 6b can now move radially inward as far as the spring arms 16. In this state, which is shown in FIG. 4, the blocking or locking of the trigger buttons 6a, 6b has been cancelled.

To now trigger an insertion movement of the infusion set 2, in which the infusion set 2, starting from the first position shown in FIGS. 3 and 4, is driven downward by the force of the spring 3 such that the infusion cannula 5 penetrates into the body 11 of the patient, the two trigger buttons 6a, 6b are pressed radially inward, entraining the spring arms 16 with them, until the locking lugs 15 of the spring arms 16 disengage from the locking shoulders 8 of the thrust element 4, and the thrust element 4, with the infusion set 2 received in it, shoots or moves rapidly downward toward the skin of the patient, driven by the force of the spring 3. The situation at the start of this insertion movement is shown in FIG. 5.

As will be seen, the infusion set 2 has a fixing plaster 18 on its underside. This fixes it upon application to the patient's skin, such that, during the subsequent lifting of the insertion device from the body 11 of the patient, the infusion set 2 detaches itself from the receptacle 12 in the thrust element 4 and remains in the applied position on the body 11 of the patient.

When the trigger buttons 6a, 6b are released again after the insertion device has been lifted from the body 11 of the patient, they move radially outward again, driven by restoring springs (not shown). The securing slide 7, driven by the restoring spring 13, then moves back again to its securing position shown in FIGS. 1 to 3. The insertion device is now once more in the state shown in FIG. 1 and can be used again for application of an infusion set 2.

Another embodiment of an insertion device according to the present invention is shown in partial vertical section in FIGS. 6 to 13, in different states that arise during its intended use, FIG. 10 showing a perspective view of the insertion device, partly in vertical section.

As can be seen from FIGS. 6 and 7, which show the insertion device without an insertion head, on the one hand in the non-pretensioned state (FIG. 6) and on the other hand in a pretensioned state (FIG. 7), this insertion device comprises a housing formed by two housing parts 1a, 1b that can be pushed together. It further comprises a thrust element 4 mounted in the upper housing part 1b in such a way as to be vertically displaceable by two mechanically synchronized pivot lever pairs 19a, 19b, and, for each pivot lever pair 19a, 19b, a energy-storing element which is formed as a torsion spring or leg spring 3 and engages on the respective pivot lever pair 19a, 19b so as to drive the thrust element 4 forward. As can be seen from FIG. 7, in which the thrust element 4 is arranged in the upper housing part 1b with the torsion springs 3 pretensioned, the upper housing part 1b, for temporary force-fit retention of the insertion head which is to be applied with the insertion device and which in this example is also designed as an infusion set 2, comprises two opposite spring shackles 12 (only one of them is visible) which are fixed to the housing and serve as a retention means between which the infusion set 2 can be held, e.g. by clamping. The infusion set 2 is in this case therefore held fixed in the upper housing part 1b, and, in contrast to the preceding illustrative embodiment, is not movable relative to the housing in the thrust element 4. As can be seen from FIG. 6, the thrust element 4 here lies with two jibs 20a, 20b on support faces of the lower housing part 1a, such that, when the two housing halves 1a, 1b are pushed together starting from the position shown in FIG. 6, it is pushed counter to the force of the torsion springs 3 into the upper housing part 1b, and the locking lug 15 of a spring arm 16 arranged on its top face engages with a locking shoulder 8 in the upper housing part 1b. In this situation, which is shown in FIG. 7, the torsion springs 3 and the thrust element 4 driven by them are made ready in a pretensioned state.

A suitable infusion set 2 can now be fitted into the insertion device and can be secured in the upper housing part 1b by being clamped between the two spring shackles 12. This situation is shown in FIG. 8.

As can be seen from a comparison with FIGS. 9 and 10, which show the insertion device according to FIG. 8 after a subsequent drawing apart of the two housing parts 1a, 1b with an infusion set 2 ready for application, the present infusion set 2 comprises an infusion cannula 5 that can be folded out. As can be seen from FIG. 8, the infusion cannula 5 is arranged hidden inside the two-part housing of the infusion set 2 upon introduction of the infusion set 2 into the pretensioned insertion device. If the two housing parts 1a, 1b of the insertion device are now drawn apart again, starting from the situation shown in FIG. 8, the two-part housing of the infusion set 2 is pushed together and the infusion cannula 5 is folded out by an internal mechanism. This situation, in which the infusion set 2 is located in a first position, is shown in FIGS. 9 and 10. The two-part housing of the infusion set 2 is pushed together by an inclined ramp surface 21 on the lower housing part 1a being displaced vertically relative to a horizontally displaceable abutment element 22, which is connected in terms of movement to the left-hand part of the two-part housing of the infusion set 2, as a result of which the left-hand part of the two-part housing is pushed into the latter's right-hand housing part.

As can also be seen from a comparison of FIGS. 8, 9 and 10, during the aforementioned drawing apart of the two housing parts 1a, 1b of the insertion device, after pretensioning of the latter, an internal locking slide 23 is coupled to the lower housing part 1a, by locking lugs 24, which are formed by spring arms 25 on the locking slide 23 and were previously arranged vertically displaceably in vertical guide slots 26 inside the lower housing part 1a, coming into engagement with locking shoulders 27 of the lower housing part 1a. In its securing position shown in FIGS. 6 to 10, the locking slide 23 blocks the actuation of an actuation member designed as trigger button 6 on the insertion device, since a securing shoulder 29 of the locking slide 23 makes it impossible for a guide ram 28, connected rigidly to the trigger button 6, to move in the actuation direction.

By the above-described engagement of the locking slide 23 with the lower housing part 1a of the insertion device, it is now possible, by renewed and partial pushing-together of the two housing parts 1a, 1b of the insertion device, to displace the locking slide 23 relative to the upper housing part 1b in such a way that the securing shoulder 29 frees the guide ram 28 for displacement in the actuation direction of the trigger button 6, such that the blocking of the trigger button 6 is cancelled. The fact that the locking slide 23 has only a relatively small displacement travel means that, in this state, it is at the same time guaranteed that the two housing parts 1a, 1b cannot be pushed so far together that the infusion cannula 5 protrudes beyond the contact faces 10, which might lead to a risk of injury. This situation is shown in FIG. 11, in which the partial pushing together of the two housing parts 1a, 1b, which permits the displacement of the locking slide 23 and therefore the release of the trigger button 6, is achieved by pressing the insertion device onto the body 11 of a patient via the contact faces 10 formed on the underside of the lower housing part 1a. After the engagement with the securing slide 23, the lower housing part 1a thus forms a first actuation member 7.

Figure 12:
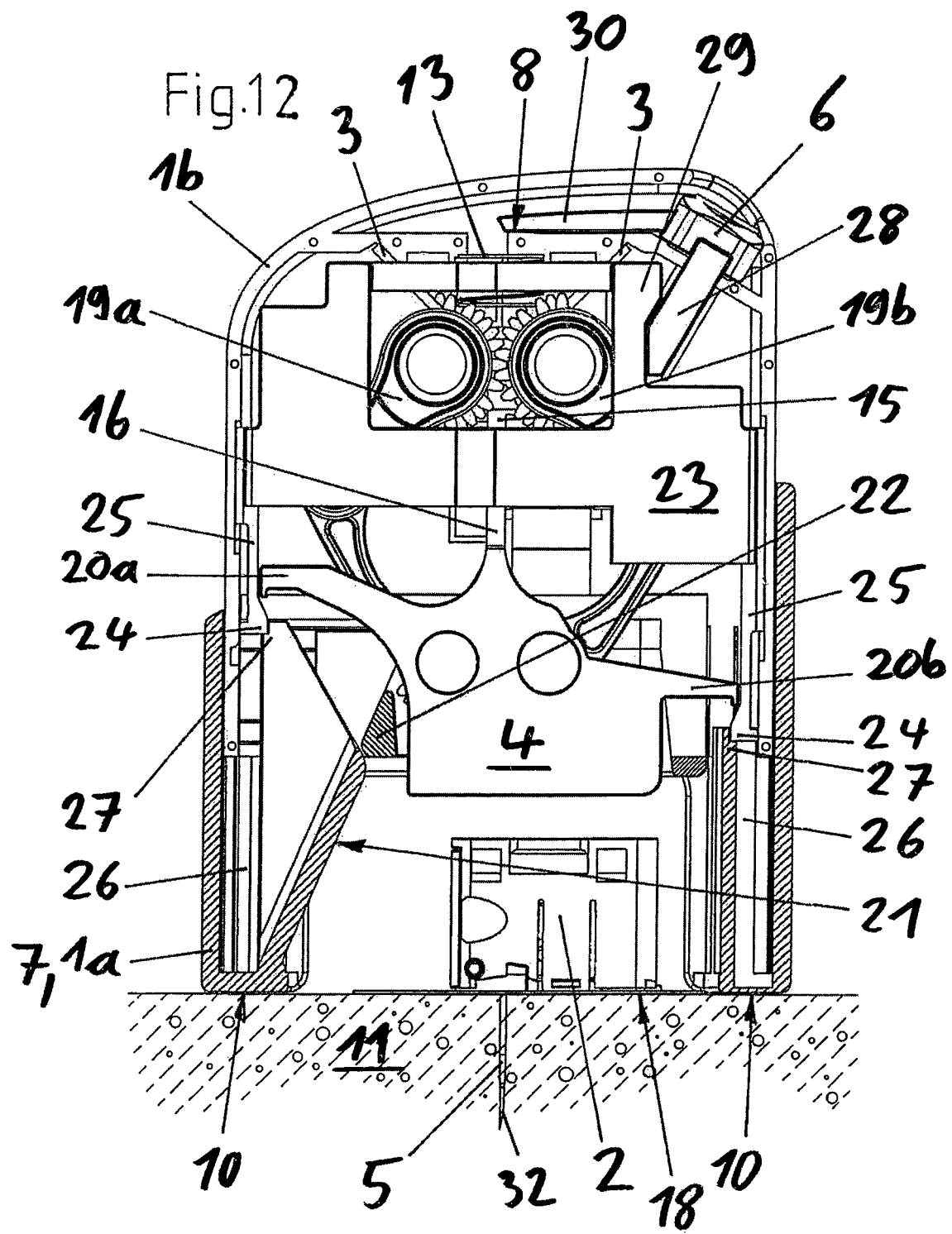
FIG. 12 is a view of the insertion device of FIG. 11, but directly after the application of the insertion head to the body of the patient.
Figure 13:
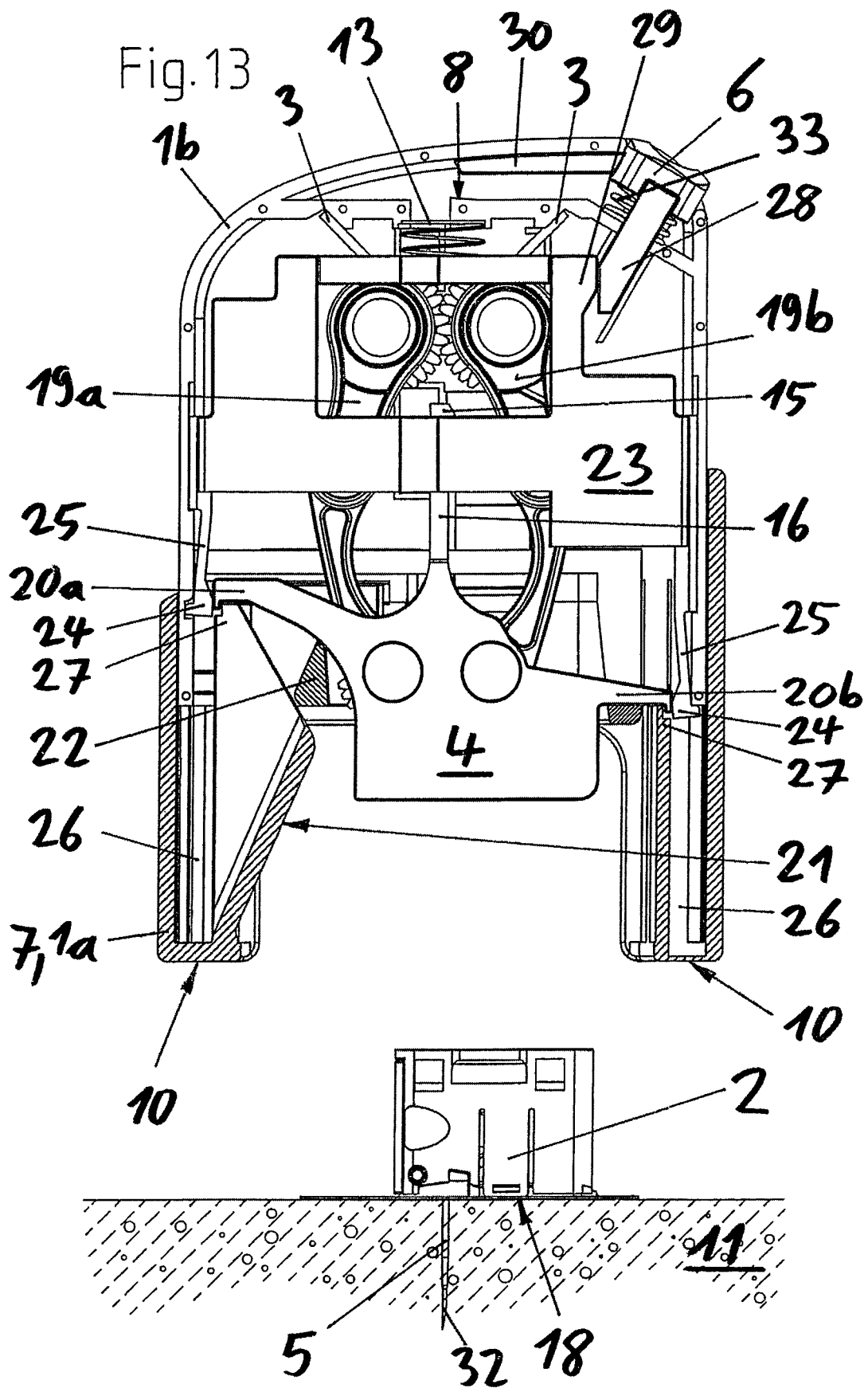
FIG. 13 is a view of the insertion device of FIG. 12, but upon removal from the body of the patient.

If the trigger button 6 is now pressed in the situation shown in FIG. 11, the trigger ram 30 presses the locking lug 15 of the thrust element 4 to the left, under elastic bending of the spring arm 16, until the locking lug 15 disengages from the locking shoulder 8 of the upper housing part 1b, and the thrust element 4 shoots downwards, guided by the two pivot lever pairs 19a, 19b and driven by the force of the pretensioned torsion springs 3. In doing so, the thrust element forcibly hits the infusion set 2 held between the spring shackles 12 and catapults it onto the application site with complete insertion of the infusion cannula 5 into the body 11 of the patient, while the fixing plaster 18 arranged on its underside simultaneously fixes it to the skin of the patient. This situation, in which the infusion set 2 is already separated from the insertion device, is shown in FIG. 12. If the insertion device is now removed from the body 11 of the patient and the actuation of the trigger button 6 is cancelled, the trigger button 6, under the effect of a restoring spring 33 (shown only in FIGS. 6, 9, 11 and 13), goes back to its non-actuated starting position, and the locking slide 23 is displaced, by an associated restoring spring 13, back to its original securing position since the insertion device is no longer being pressed with force onto the body 11, with the two housing parts 1a, 1b being completely drawn apart. At the same time, the locking lugs 24 of the locking slide 23 are pressed outward by the jibs 20a, 20b of the thrust element 4, with elastic bending of the spring arms 25, until they disengage from the locking shoulders 27 of the lower housing part 1a. This situation directly after the insertion device has been lifted from the body 11 of the patient is shown in FIG. 13. The insertion device is now once more in the original state shown in FIG. 6, and it can be used again for application of an infusion set 2.

It will generally be noted that, in both the first and second illustrative embodiments, insertion heads are shown which are designed as infusion sets 2 with a flexible cannula 5 (soft cannula), said flexible cannulas being supported in each case by a guide needle 32. After application, these guide needles 32, together with a component of the originally applied infusion set 2 connected to them, are removed (not shown here), and an infusion line is then connected to the remaining applied infusion set 2 for the purpose of delivering an infusion liquid into the body 11 of the patient.

Figure 14:
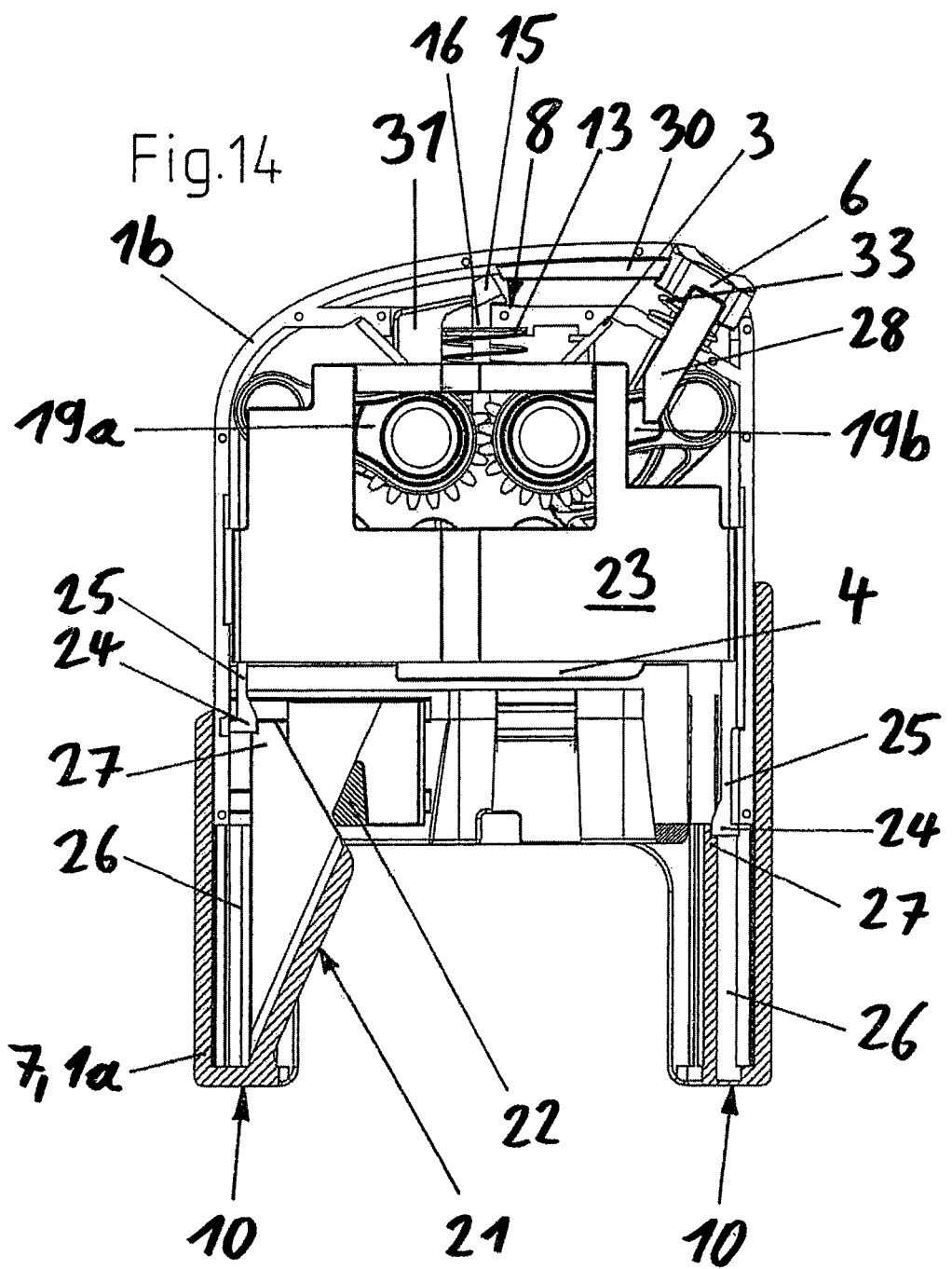
FIG. 14 is a partial vertical section through another embodiment of an insertion device according to the present invention for insertion heads, in the pretensioned and secured state, without an insertion head.
Figure 15:
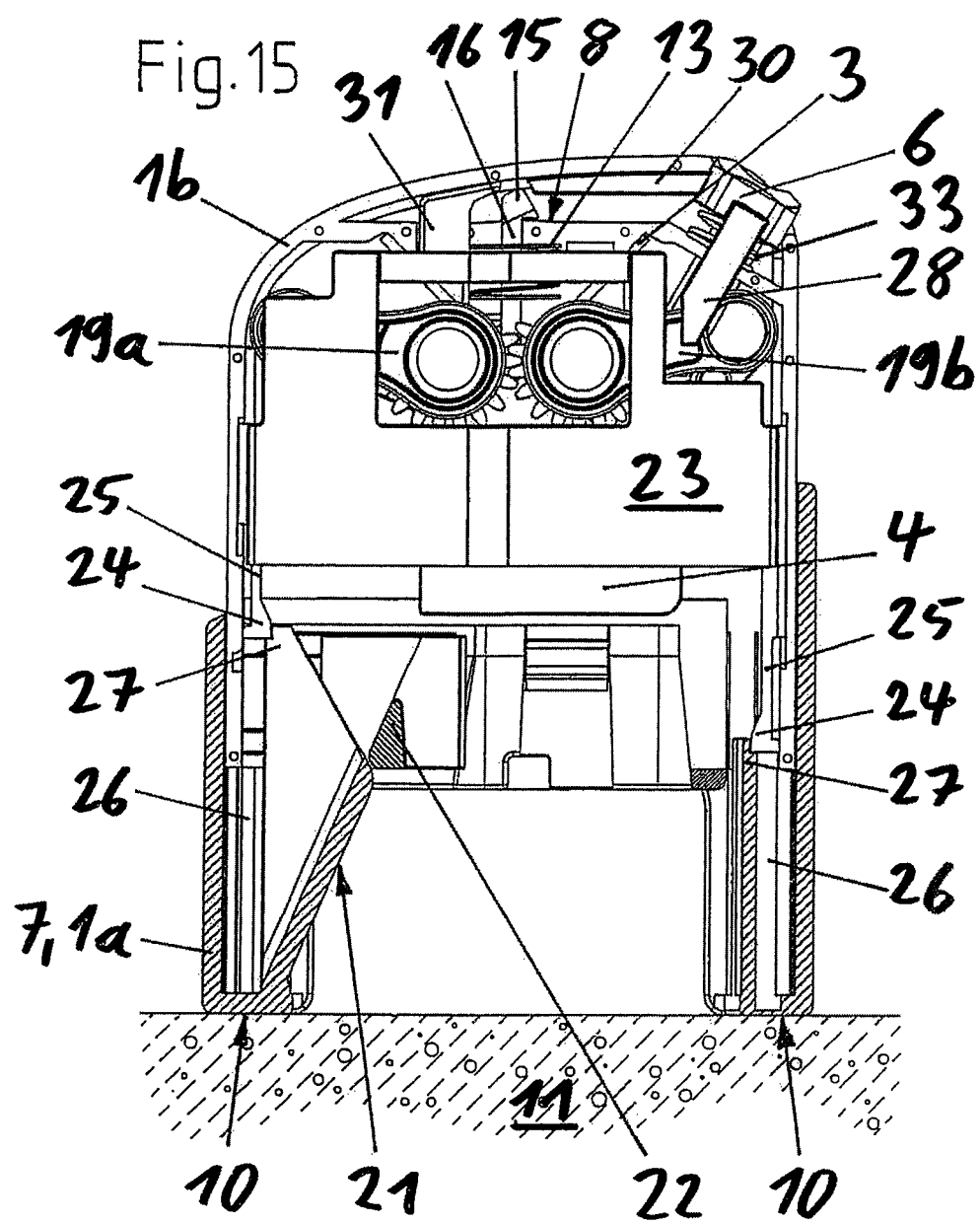
FIG. 15 is a view of the insertion device of FIG. 14, but in the released state, when placed and pressed onto the body of a patient.

FIGS. 14 and 15 show another embodiment of the insertion device according to the present invention in partial vertical section, first in the pretensioned and secured state, and second in the released state when placed and pressed onto the body 11 of a patient. This embodiment generally corresponds to the second embodiment shown in FIGS. 6 to 13, and the operating states shown correspond to the states shown in FIGS. 9 and 11, except that, to simplify the illustration, no insertion head is shown here in the insertion device.

A difference between the embodiment of FIGS. 14 and 15 and the above-described second embodiment is that the actuation button 6 is in this case not blocked by its guide ram 28 being blocked by the locking slide 23. Instead the deflection of the spring arm 16 of the thrust element 4 is cancelled by an abutment element 31 formed on the locking slide 23, as long as the locking slide 23 is located in the securing position, such that its locking lug 15 cannot be disengaged from the locking shoulder 8 of the upper housing part 1b. This situation is shown in FIG. 14. If, as has already been described in the preceding example, the locking slide 23 is now displaced upward in the upper housing part 1b by the insertion device being pressed via the contact faces 10 of the lower housing part 1a onto the body 11 of a patient, the abutment element 31 frees the spring arm 16, such that the locking lug 15 thereof can be disengaged from the locking shoulder 8 by pressing the actuation button 6, so as to trigger the insertion device. All the other functions and modes of operation are identical to those described in connection with the second illustrative embodiment.

Figure 16:
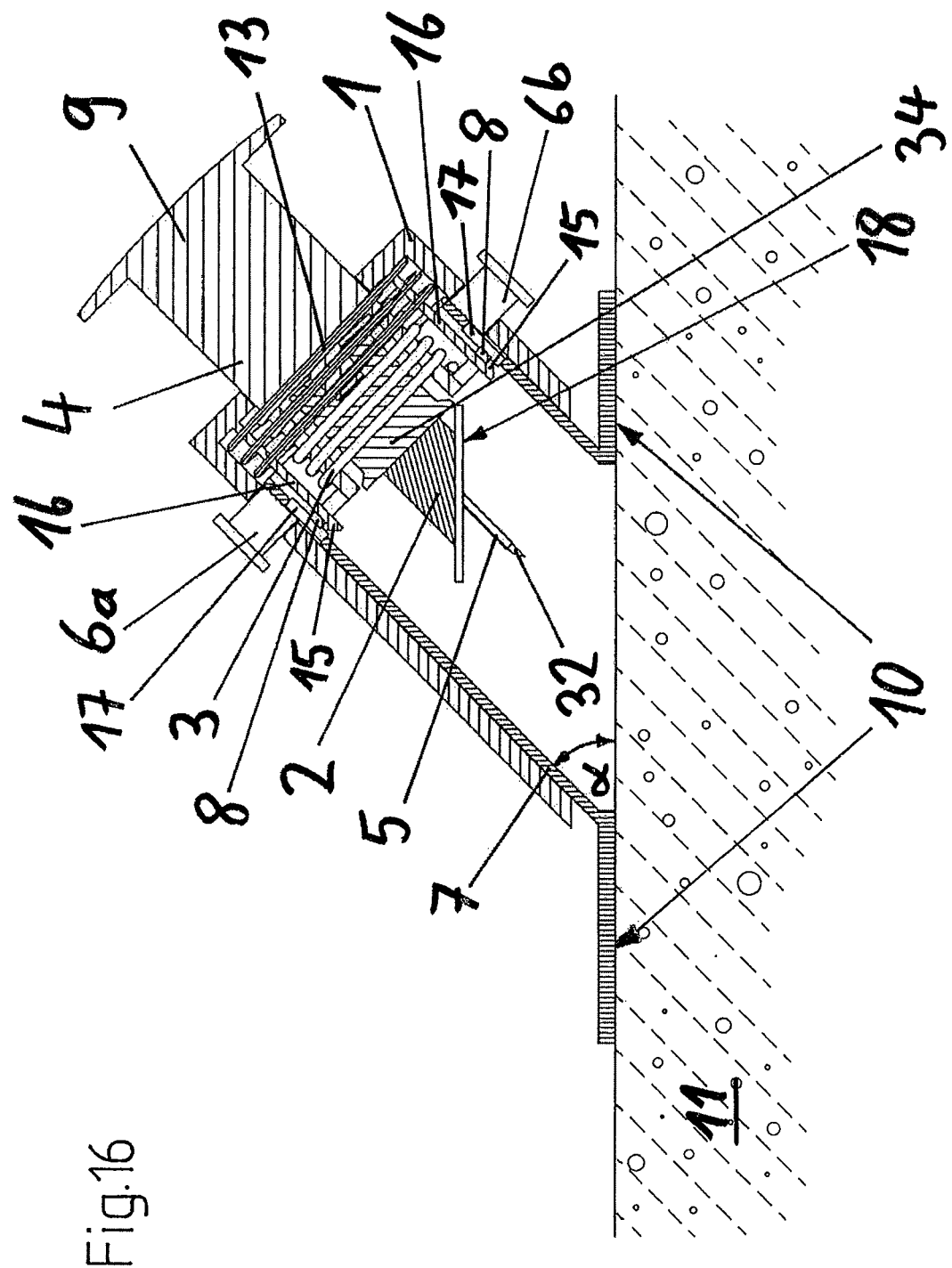
FIG. 16 is a vertical section through another embodiment of an insertion device according to the present invention in the pretensioned state, with an insertion head arranged in it in the secured state.

FIG. 16 shows a vertical section through another embodiment of an insertion device according to the present invention in the pretensioned state, with an infusion set 2 arranged in it in the secured state. The insertion device of this embodiment differs from the insertion device of the FIGS. 1 to 5 in that it is adapted for the inclined application of an infusion set especially adapted for such an application, i.e. the direction of introduction of the cannula 5 and of the guide needle 32 forms together with the skin surface at the application site an angle α smaller than 90°. In some preferred embodiments, this angle α may be in the range between 20° and 45°. In the illustrated embodiment, it is 45°. For this, the housing 1 and the securing slide 7 of the insertion device shown in the FIGS. 1 to 5 have been modified. A further difference consists in the interface between the thrust element 4 and the infusion set 2, which in the present case is formed by an adapter 34. All other components and the operation of the device are identical to those of the device of the FIGS. 1 to 5, thus, for a detained description thereof reference is made to the description of the FIGS. 1 to 5.

Figure 17:
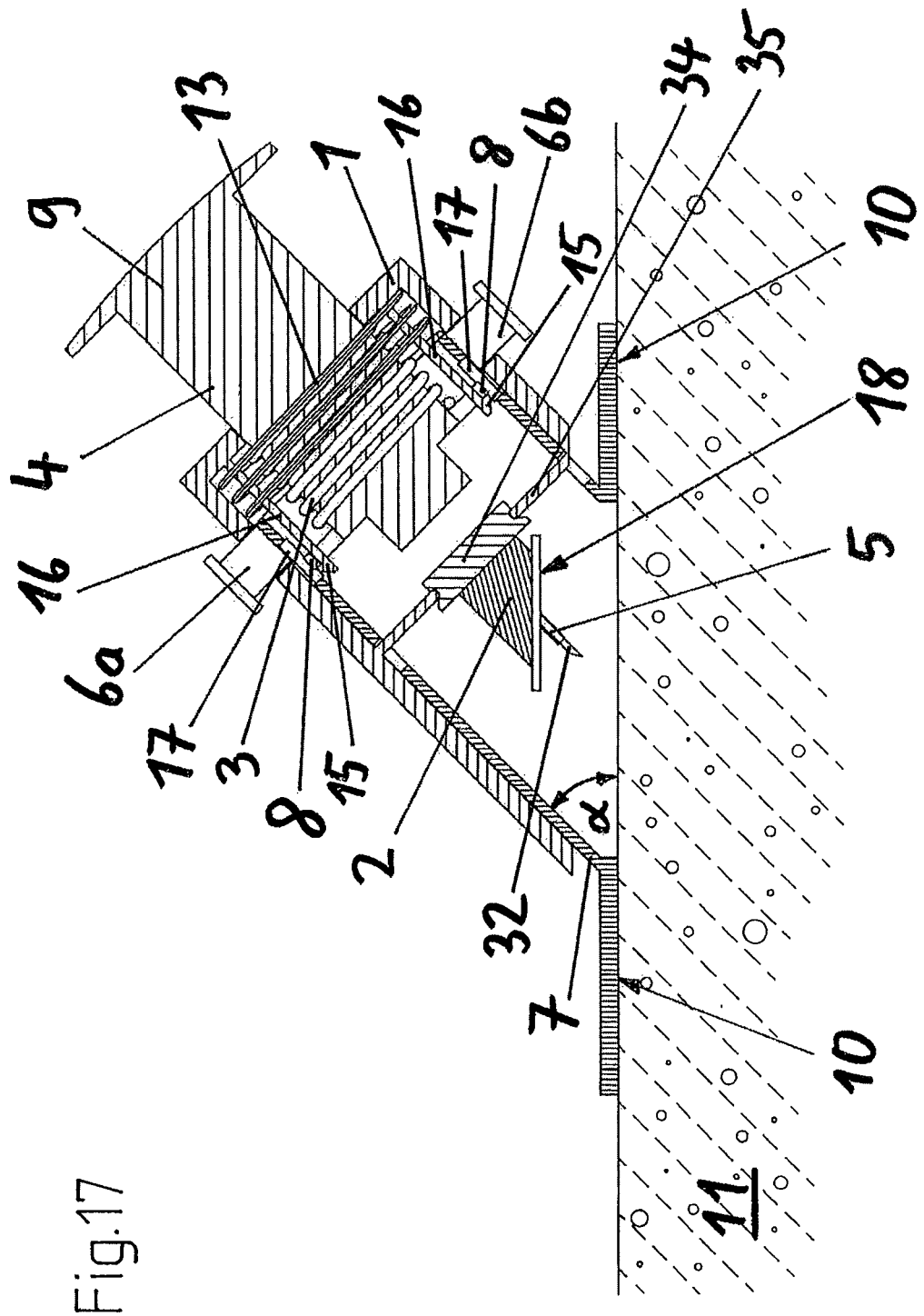
FIG. 17 is a vertical section through another embodiment of an insertion device according to the present invention in the pretensioned state, with an insertion head arranged in it in the secured state.

FIG. 17 shows a vertical section through another embodiment of an insertion device according to the present invention in the pretensioned state, with an infusion set 2 arranged in it in the secured state. This insertion device differs from the insertion device of FIG. 16 in that the infusion set 2 is not attached to the thrust element 4 but is held by an adapter 34 and a frame 35 in the housing 1 of the insertion device. The adapter 34 in this embodiment basically is a disc-shaped element with a circumferential groove.

When the thrust element 4, which at its face forms a hammer, upon release and actuation of the trigger buttons 6a, 6b, is driven downward by the force of the spring 3, it forcibly hits the adapter 34, thereby detaches it from the frame 35 and catapults the adapter 34 with the infusion set 2 onto the application site, thereby completely inserting the cannulla 5 with the insertion needle 32 into the body 11 of the patient.

Figure 18:
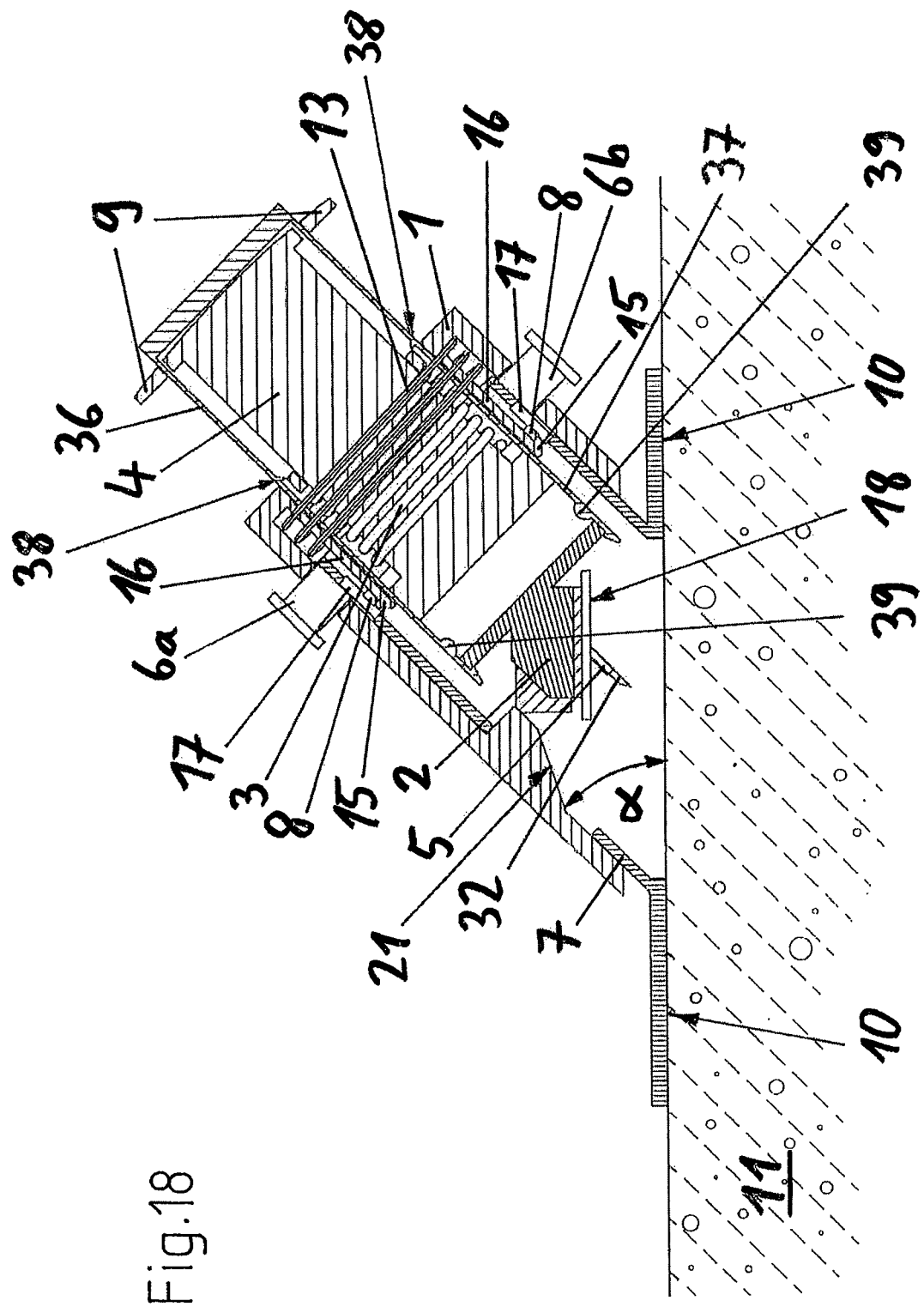
FIG. 18 is a vertical section through another embodiment of an insertion device according to the present invention in the pretensioned state, with an insertion head arranged in it in the secured state.

FIG. 18 shows a vertical section through another embodiment of an insertion device according to the present invention in the pretensioned state, with an infusion set 2 arranged in it in the secured state. This insertion device differs from the insertion device of FIG. 16 in that it is adapted for infusion sets 2 with tiltable cannula 5 and insertion needle 32, which in the situation illustrated in FIG. 18 have already been tilted from a folded-in state, in which the cannula 5 and the insertion needle 32 are hidden inside the housing of the infusion set 2, into the shown folded-out state.

As can be seen in the drawing, the infusion set 2 in this embodiment is not attached to the thrust element 4 but is held by a clamping sleeve 36 which holds the infusion set 2 by several spring arms 37. The thrust element 4 is arranged within the clamping sleeve 36 and with two grip parts 9 radially protrudes through the sleeve 36.

In the loading position (not shown), the clamping sleeve 36 together with the thrust element 4 is in a foremost position within the housing 1. After the infusion set 2 is attached to the clamping sleeve 36, the thrust element 4 and the clamping sleeve 36 are by means of the grip parts 9 retracted until the clamping sleeve 36 engages at the housing 1 with catches 38 formed at its inner side.

During this movement of the clamping sleeve 36, the two-part housing of the infusion set 2 is pushed together by an inclined ramp surface 21 arranged at the inner side of the housing 1, whereby the infusion cannula 5 and the insertion needle 32 are folded out by an internal mechanism of the infusion set 2.

When the thrust element 4, upon release and actuation of the trigger buttons 6a, 6b, is driven downward by the force of the spring 3, it spreads the spring arms 37 by contacting cam elements 39 arranged at the inner sides thereof, thereby releasing the infusion set 2, and forcibly hits the infusion set 2 and catapults it onto the application site. By this, the cannulla 5 with the insertion needle 32 is completely inserted into the body 11 of the patient.

Although the insertion heads to be applied in the above illustrative embodiments are designed as infusion sets, it should once again be clearly noted that the insertion devices shown are also suitable for the application of other insertion heads, for example heads designed as a port or sensor arrangement or as a combination of a sensor arrangement and a port or infusion set, and that the invention is suitable for any conceivable insertion heads that can be applied by introducing a needle-like or blade-like element into the body of a patient.

It should also be noted that combinations of the technical solutions and/or structures set out in the illustrative embodiments hereof are also envisaged, for example an insertion device according to the first illustrative embodiment shown in FIGS. 1 to 5, but in which the insertion head is not held in the thrust element but instead, as is shown in the second illustrative embodiment according to FIGS. 6 to 13, is held separate from the thrust element in the housing.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An insertion device for an insertion head with at least one of an infusion cannula or a puncturing tip for introduction into the body of a patient, the insertion device comprising:
   a housing;
   at least one contact face for placing on an application site on the body of the patient for application of the insertion head;
   retention means with which the insertion head that is to be applied is temporarily held on the insertion device;
   a drive mechanism configured to supply a drive force for effecting an insertion movement of the insertion head relative to the contact face from a first position in which the insertion head is held by the retention means such that the infusion cannula or the puncturing tip is set back relative to the contact face to a second position in which the infusion cannula or the puncturing tip protrudes beyond the contact face to permit introduction of the infusion cannula or of the puncturing tip into the body of the patient when the insertion movement is executed with the contact face of the insertion device placed on the body;
   a first actuation member slidably coupled to the housing, wherein the contact face forms a distal end of the first actuation member; and a second actuation member;
wherein the first and second actuation members have to be actuated sequentially to trigger the insertion movement, wherein the first actuation member has at least one opening adjacent an end opposite the distal end, and the second actuation member can only be actuated while the first actuation member is actuated by the contact face being pressed against the body of the patient such that it is slid relative to the housing so as to bring the at least one opening into alignment with the second actuation member and permit the second actuation member to move radially inward through the opening to be actuated.

2. The insertion device according to claim 1, wherein, when the pressing actuating force ceases, the actuation members automatically go back to an unactuated state.

3. The insertion device according to claim 1, wherein the first actuation member is one of a slide-shaped or button-shaped element, which comprises the contact face.

4. The insertion device according to claim 3, wherein the second actuation member is a button-shaped element which, when a user presses it with a finger tip is actuated transversely to the direction in which the insertion device is pressed onto the body of the patient.

5. The insertion device according to claim 1, wherein the actuation members are actuable with one hand to permit one-handed triggering of the insertion movement.

6. The insertion device according to claim 1, wherein the drive mechanism comprises at least one energy-storing element for providing the drive energy for the insertion movement.

7. The insertion device according to claim 6, wherein the at least one energy storing element is selected from a group consisting of a helical spring, leg spring or leaf spring made of metal or rubber.

8. The insertion device according to claim 6, wherein the at least one energy-storing element can be tensioned repeatedly by a user.

9. The insertion device according to claim 8, wherein the drive mechanism comprises a thrust element for transmitting the drive energy to the insertion head and wherein by displacing the thrust element counter to the direction of the insertion movement and subsequently locking it with locking means that can be released by the actuation members the energy-storing element is tensioned.

10. The insertion device according to claim 9, wherein the insertion the thrust element is connected to a grip part which can be grasped by hand and which is movable relative to the housing for tensioning the energy-storing element.

11. The arrangement according to claim 1, wherein the insertion device is configured such that the second actuation member is blocked from performing an actuating movement until the first actuation element is slid relative to the housing in a direction counter to the insertion movement.

12. An arrangement comprising an insertion device and an insertion head receiveable in said insertion device, the insertion device comprising:
a) at least one contact face for placing the insertion device on an application site on the body of the patient for application of the insertion head;
b) a retainer with which the insertion head that is to be applied is temporarily held on the insertion device;
c) a drive for automatically effecting an insertion movement of the insertion head relative to the contact face from a first position in which the insertion head is held by the retainer such that an infusion cannula or a puncturing tip is set back relative to the contact face to a second position in which the infusion cannula or the puncturing tip protrudes beyond the contact face to permit introduction of the infusion cannula or of the puncturing tip into the body of the patient when the insertion movement is executed with the contact face of the insertion device placed on the body; and
d) at least two actuation members which have to be actuated sequentially to trigger the insertion movement, wherein a first of the actuation members is actuated by the contact face being pressed onto the body of the patient and a second of the actuation members is actuated by a movement that is independent of said pressing onto the body of the patient, and wherein the first of the actuation members has at least one opening adjacent an end opposite the contact face, and the second of the actuation members can only be actuated while the first of the actuation members is actuated by the contact face being pressed against the body of the patient so as to bring the at least one opening into alignment with the second of the actuation members and permit the second of the actuation members to move radially inward through the opening to be actuated.

13. The arrangement according to claim 12, wherein the second actuation member is actuated by the user applying a force to the second actuation member with a finger tip in a direction substantially transverse to the direction in which the insertion device is pressed onto the body of the patient.

14. The arrangement according to claim 12, wherein the drive comprises an energy-storing element.

15. An insertion device for applying an infusion set to the body of a patient, the device comprising two actuation members which have to be actuated sequentially to trigger an insertion movement of the infusion set, wherein a first one of the actuation members is a securing slide including a contact face to be placed on the body of the patient, the securing slide being actuated by the insertion device being pressed, via the contact face, against the body of the patient, and wherein the first of the actuation members has at least one opening adjacent an end opposite the contact face, and a second one of the actuation members can only be actuated while the first one of the actuation members is actuated by the contact face being pressed against the body of the patient so as to bring the at least one opening into alignment with the second of the actuation members and permit the second of the actuation members to move radially inward through the opening to be actuated.

16. A method for applying an insertion head to the body of a patient using an insertion device, wherein the insertion head is one of an infusion set, port or sensor arrangement and the insertion device comprises at least one contact face for placing the insertion device on an application site on the body of the patient for application of the insertion head, a retainer with which the insertion head that is to be applied is temporarily held on the insertion device, a drive for effecting an insertion movement of the insertion head relative to the contact face from a first position in which the insertion head is held by the retainer such that an infusion cannula or a puncturing tip is set back relative to the contact face to a second position in which the infusion cannula or the puncturing tip protrudes beyond the contact face to permit introduction of the infusion cannula or of the puncturing tip into the body of the patient when the insertion movement is executed with the contact face of the insertion device placed on the body; and at least two actuation members which have to be actuated sequentially to trigger the insertion movement, wherein a first of the actuation members is designed such that it can be actuated by the contact face being pressed onto the body of the patient, wherein the first of the actuation members has at least one opening adjacent an end opposite the contact face, and the second of the actuation members can only be actuated while the first of the actuation members is actuated by the contact face being pressed against the body of the patient so as to bring the at least one opening into alignment with the second of the actuation members and permit the second of the actuation members to move radially inward through the opening to be actuated, the method comprising the following steps:
 a) placing an insertion head with an infusion cannula or a puncturing tip into the retainer in the first position;
 b) arranging and pressing the insertion device via the contact face onto the desired application site on the body of the patient such that the infusion cannula or the puncturing tip of the insertion head can penetrate into the body during the insertion movement and actuating the first actuation member; and
 c) while pressing the contact face against the body of the patient sufficiently to slide the contact face relative to the housing such to bring the at least one opening into alignment with the second of the actuation members to permit the second of the actuation members to move radially inward through the opening to be actuated, and actuating the second and, if present, any further actuation members for triggering the insertion movement.

17. The method according to claim 16, wherein the arranging and pressing of the insertion device and the actuating of the second and, if present, also any further actuation members is done with one hand.

18. The method according to claim 17, wherein the insertion device is pressed onto the desired application site in the direction of the insertion movement.

19. The method according to claim 18, wherein the second and, if present, any further actuation members are each actuated by the user pressing with a finger tip in a direction transverse to the direction in which the insertion device is pressed onto the body of the patient.

\* \* \* \* \*

UNITED STATES PATENT AND TRADEMARK OFFICE
CERTIFICATE OF CORRECTION

PATENT NO. : 8,870,822 B2
APPLICATION NO. : 12/391513
DATED : October 28, 2014
INVENTOR(S) : Christian Thalmann et al.

It is certified that error appears in the above-identified patent and that said Letters Patent is hereby corrected as shown below:

IN THE SPECIFICATION

Col. 11, Line 14,
"a smaller than 90°. In some preferred embodiments, this angle" should read
--α smaller than 90°. In some preferred embodiments, this angle--;

Col. 11, Line 22,
"of the device of the FIGS. 1 to 5, thus, for a detained descrip-" should read
--of the device of the FIGS. 1 to 5, thus, for a detailed descrip- --;

IN THE CLAIMS

Col. 13, Claim 9, Line 44,
"that can be released by the actuation members the energy" should read
--that can be released by the actuation members where the energy--; and Col. 13, Claim 10, Line 47,
"insertion the thrust element is connected to a grip part which" should read
--insertion of the thrust element is connected to a grip part which--.

Signed and Sealed this
Twenty-ninth Day of December, 2015

Michelle K. Lee
*Director of the United States Patent and Trademark Office*